(12) United States Patent
Winter et al.

(10) Patent No.: US 12,117,450 B2
(45) Date of Patent: Oct. 15, 2024

(54) DNA-CAGE ERASABLE LABELS FOR FLUORESCENCE-BASED PATHOLOGY

(71) Applicant: Ohio State Innovation Foundation, Columbus, OH (US)

(72) Inventors: Jessica Winter, Columbus, OH (US); Elizabeth Jergens, Columbus, OH (US); Kil Ho Lee, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 822 days.

(21) Appl. No.: 17/292,955

(22) PCT Filed: Nov. 15, 2019

(86) PCT No.: PCT/US2019/061606
§ 371 (c)(1),
(2) Date: May 11, 2021

(87) PCT Pub. No.: WO2020/102624
PCT Pub. Date: May 22, 2020

(65) Prior Publication Data
US 2022/0003773 A1    Jan. 6, 2022

Related U.S. Application Data

(60) Provisional application No. 62/825,406, filed on Mar. 28, 2019, provisional application No. 62/767,854, filed on Nov. 15, 2018.

(51) Int. Cl.
*C12Q 1/68* (2018.01)
*G01N 33/543* (2006.01)
*G01N 33/58* (2006.01)

(52) U.S. Cl.
CPC ..... *G01N 33/585* (2013.01); *G01N 33/54393* (2013.01); *G01N 2458/10* (2013.01)

(58) Field of Classification Search
None
See application file for complete search history.

(56) References Cited

U.S. PATENT DOCUMENTS

2014/0255307 A1*  9/2014  Ahn ............... A61K 49/0032
                                                        424/9.1
2015/0204857 A1   7/2015  Clarke
                          (Continued)

FOREIGN PATENT DOCUMENTS

WO       2016081060 A2    5/2016

OTHER PUBLICATIONS

International Search Report issued for PCT/US2019/061606, mailed Feb. 11, 2020.
(Continued)

*Primary Examiner* — Aaron A Priest
(74) *Attorney, Agent, or Firm* — Thomas | Horstemeyer, LLP

(57) ABSTRACT

Disclosed herein are erasable label systems that involve nanocage molecules positioned around nanoparticles, which can be loaded with, bound to, or adsorbed with imaging agents. The nanocages can contain targeting arms composed of ssDNA or ssRNA that can be used to target biomolecules. For DNA or RNA targeting, this can be done directly. Antibodies can be targeted using avidin-biotin coupling to ssDNA or direct ssDNA conjugation to the antibody surface. ssDNA or ssRNA complementary to one of the arms can then be used to "erase" the label.

9 Claims, 15 Drawing Sheets
Specification includes a Sequence Listing.

(56) References Cited

U.S. PATENT DOCUMENTS

| | | | |
|---|---|---|---|
| 2018/0016569 A1* | 1/2018 | Fu | C12N 11/04 |
| 2019/0008963 A1* | 1/2019 | Han | C07H 21/00 |
| 2019/0062830 A1 | 2/2019 | Nikiforov et al. | |
| 2019/0127739 A1* | 5/2019 | Guo | C12N 15/117 |
| 2019/0178879 A1 | 6/2019 | Clarke et al. | |
| 2020/0385734 A1* | 12/2020 | Chang | A61K 39/0011 |
| 2022/0331453 A1* | 10/2022 | Lim | C07K 16/28 |

OTHER PUBLICATIONS

Dubertret et al., In Vivo Imaging of Quantum Dots Encapsulated in Phospholipid Micelles, Science, vol. 298, p. 1759-1762, 2002.

Jiang et al., Nanoparticle-programmed surface for drug release and cell regulation via reversible hybridization reaction, ACS Appl Mater Interfaces., 9(5) p. 4467-4474, 2017.

* cited by examiner

DNA-CAGE ERASABLE LABELS FOR FLUORESCENCE-BASED PATHOLOGY

CROSS-REFERENCE TO RELATED APPLICATIONS

This application is a National Stage of International Application No. PCT/US2019/061606, filed Nov. 15, 2019, which claims benefit of U.S. Provisional Application No. 62/767,854, filed Nov. 15, 2018, and U.S. Provisional Application No. 62/825,406, filed Mar. 28, 2019, which are hereby incorporated herein by reference in their entireties.

STATEMENT REGARDING FEDERALLY SPONSORED RESEARCH OR DEVELOPMENT

This invention was made with Government Support under Grant No. DE-SC0017270 awarded by the Department of Energy, and under Grant No. 1555470 awarded by the National Science Foundation. The Government has certain rights in the invention.

SEQUENCE LISTING

This application contains a sequence listing filed in electronic form as an ASCII.txt file entitled "321501_2390_Sequence_Listing_ST25" created on Nov. 14, 2019. The content of the sequence listing is incorporated herein in its entirety.

BACKGROUND

Histopathology is a cornerstone of tissue analysis method used to diagnose many clinical conditions. Often these diagnoses are based on the presence of specific biomarkers indicated by colored or fluorescent labels. Current state of the art primarily relies on colorimetric measurement of biomarkers using colored dye molecules. Only 1-2 markers can be analyzed on the same slide using this approach. However, the advancement of personalized medicine will require labeling of multiple (10 or more) biomarkers simultaneously. Thus, additional technologies are needed to enable application of pathology to personalized medicine.

In contrast, fluorescence microscopy is a standard method of analysis in biomedical research to analyze many markers simultaneously. In this approach, a fluorescent molecule is bound to the biomarker of interest, and depending on the number of different colors available many biomarkers can be labeled. However, even with this approach biomarker labeling is usually limited to 3-4 markers. Further, labeling in tissue presents substantial challenges over that of dispersed cells in culture because of tissue auto-fluorescence, diffusion issues, and loss of biomarker binding sites resulting from tissue processing (epitope damage).

To address these challenges, some researchers have developed 'erasable labels' that can be used to identify biomarkers, and then removed to enable repeated inquiry of the same sample. These current methods are based on two common approaches. In the first, labels are removed by bleaching label fluorescence using high intensity light. Unfortunately, this can damage the tissue. The second method uses chemicals to breakdown the fluorescent molecules, eliminating the fluorescence. This methods can also cause tissue damage.

Advances in histopathological methods are needed to quantitatively and spatially evaluate biomarkers in the context of their native environment in order to provide broadly applicable tools that enhance, complement, and extend developments in genomics and proteomics, enabling significant progress in many fields.

SUMMARY

Disclosed herein are erasable label systems that involve DNA or RNA cage molecules positioned around nanoparticles, which can be loaded with imaging agents, such as colored or fluorescent dyes or quantum dots. The DNA or RNA molecules can contain arms composed of ssDNA or ssRNA "targeting arms" that can be used to target biomolecules. For DNA or RNA targeting, this can be done directly. However, the targeting arms can also be linked to other targeting agents, such as antibodies and aptamers. For example, antibodies can be coupled directly to a single stranded "targeting oligonucleotide" that binds the ssDNA or ssRNA of the DNA cage. Alternatively, the antibody can be linked indirectly to the single stranded targeting oligonucleotide via proteins, such as avidin/streptavidin and biotin, that will complete the connection. For example, the antibody can be linked to a biotin molecule while the targeting oligonucleotide is linked to an avidin/streptavidin molecule. Likewise, the antibody can be linked to an avidin/streptavidin molecule while the targeting oligonucleotide is linked to a biotin molecule. Alternatively, both the antibody and the targeting DNA can be conjugated to biotin or avidin and the complement (avidin or biotin) used to from a molecular sandwich, Regardless of the targeting agent used, all of the disclosed embodiments allow for the use of a single stranded oligonucleotide "erasing molecule" that has greater complementary to either the targeting arms of the DNA or RNA cage or to the targeting oligonucleotide, which when present will "erase" the label. As shown in the Examples, this approach can provide repeated, erasable behavior of greater than 70% signal.

In some of these embodiments, the targeting arms of the DNA or RNA cage have a nucleic acid sequence that is at least partially complementary to both the targeting oligonucleotide and the erasing molecule but has a higher complementarity and affinity for the erasing molecule.

In some of these embodiments, the targeting oligonucleotide is at least partially complementary to both the targeting arms of the DNA or RNA cage and the erasing molecule but has a higher complementarity and affinity for the erasing molecule.

Therefore, disclosed herein is a labeling system that involves a nanoparticle loaded with or conjugated to a one or a plurality of imaging (e.g. fluorescent or colored) labels that is encapsulated by a DNA or RNA nanocage comprising targeting arms, which may also be conjugated to imaging labels. In some cases, these targeting arms are themselves targeting agents that bind DNA or RNA targets. In other embodiments, the system also involves an additional targeting agent, such as an antibody or aptamer, that is conjugated directly or indirectly to single stranded oligonucleotide(s) that binds the targeting arms of the DNA or RNA nanocage. The system also involves ssDNA erasing molecule(s) that are able to compete for binding between the targeting arm of the DNA or RNA nanocage and the target molecule to dissociate them and thereby erase the signal.

The targeting agent can be any molecule that directly or indirectly binds a target in a sample or subject. For example, the targeting agent can be a primary or secondary antibody, or fragment thereof. The targeting agent can also be a DNA or RNA aptamer, a protein aptamer, protein, or a soluble receptor molecule with binding affinity for the target.

Methods for designing DNA and RNA nanocages, e.g., using DNA and RNA nanostructural techniques, including but not limited to origami, tile, or wireframe techniques, are known and adaptable in the present systems. In some embodiments, the DNA or RNA nanocage comprises a plurality of DNA or RNA oligomers, wherein each oligomer comprises at least three ssDNA or ssRNA oligonucleotides self-assembled to form at least three arms, wherein at least two of the arms terminate as ssDNA or ssRNA sticky ends that are complementary to each other, such that the nanocage comprises a plurality of the oligomers linked by the sticky ends. In some embodiments, a portion of the oligomers comprises at least arms that terminates as the ssDNA or ssRNA targeting arms. For example, about 1%, 2%, 3%, 4%, 5%, 6%, 7%, 8%, 9%, 10%, 15%, 20%, 25%, 30%, 35%, 40%, 45%, 50% or more of the total oligomers can have at least one are that terminates as the targeting arm comprises.

In other embodiments, DNA or RNA nanocages are comprised of a plurality of DNA or RNA oligomers composed of a mixture of self-assembled oligonucleotides with a predetermined number of complementary arms and those with fewer complimentary arms and some segments replaced with ssDNA or ssRNA targeting arms. In these embodiments, the nanocage is formed when a plurality of the oligomers are interlinked by the sticky ends. Alternatively, cages may be formed by steric hindrance, if the number of cage segments adsorbed or bound to the nanoparticle surface becomes sufficiently large to prevent interlocking of segments. In some embodiments, each of the DNA oligomers comprises three arms that form a planar or three dimensional structure, but other designs are suitable if they can form a cage around an ellipse, e.g. sphere.

In some embodiments, the imaging agent is a hydrophobic fluorescent or colored molecule that is attracted to or encapsulated in the hydrophobic core of a polymer nanoparticle. For example, the imaging agent can be a chromophore, fluorophore, or quantum dot (QD)). Example fluorophores include 4-Bromomethyl-7-methoxycoumarin ($\lambda$ex/em=322/395, #A5551), 4-Bromomethyl-6,7-dimethoxy-coumarin ($\lambda$ex/em=354/435, #A5570), 7,8-Dihydroxy-4-methylcoumarin ($\lambda$ex/em=395/480, #D4793), and coumarin-6 ($\lambda$ex/em=457/505 nm, #B2088) from TCI America. Example chromophores include indigo (229296, Aldrich) and Quinizarin, orange (Q906) from Aldrich. Example quantum dots include CdS/ZnS (400, 425, or 450 nm emission) and CdSe/ZnS (520, 540, 560, 580, 600, or 620 nm emission) from Ocean Nanotech.

In some embodiments, the nanoparticle is made of block copolymers such as polystyrene-b-polyethylene oxide. Other suitable nanoparticles include polylactic-co-glycolic acid, and silica nanoparticles. These nanoparticles are preferably hydrophilic on the surface and capable of being loaded with a hydrophobic imaging agent. In certain embodiments, the nanoparticle could encapsulate hydrophilic agents in a hydrophilic core, e.g., liposomes, or in interstitial space occupied by an aqueous phase, e.g., solid polymer nanoparticle.

Also disclosed herein is a method for multiplex imaging of a sample. The method involves first providing imaging systems for each target. For example, the imaging system for the first target can involve a first targeting agent that selectively binds a first target in the sample, wherein the first targeting agent is conjugated to a first oligonucleotide targeting molecule, a first nanocage assembly comprising a nanoparticle loaded with one or a plurality of imaging agents and encapsulated in a DNA or RNA nanocage, wherein the nanocage comprises a first targeting arm that selectively binds the first targeting molecule, and a first erasing molecule comprising a nucleic acid sequence that is more complementary to either the first targeting arm or the first targeting molecule; and Likewise, the second imaging system for the second target can involve a second targeting agent that selectively binds a second target in the sample, wherein the second targeting agent is conjugated to a second single stranded targeting oligonucleotide molecule; a second nanocage assembly comprising a nanoparticle loaded with one or a plurality of imaging agents and encapsulated in a DNA or RNA nanocage, wherein the DNA nanocage comprises a second targeting arm that selectively binds the second targeting molecule; and optionally a second ssDNA or ssRNA erasing molecule comprising a nucleic acid sequence that is more complementary to either the second targeting arm or the second targeting molecule. The second ssDNA or ssRNA erasing molecule is only needed if a third targeting system is going to be used.

The disclosed method involves contacting the sample with the first targeting agent under conditions suitable for the first targeting agent to selectively bind the first target in the sample and contacting the sample with the second targeting agent under conditions suitable for the first targeting agent to selectively bind the second target in the sample. These can be done together or separately.

The method then involves contacting the sample with the first nanocage assembly under conditions suitable for binding of the targeting arm of the first nanocage assembly to the targeting molecule of the first targeting agent. Once that is complete, the method can involve imaging the sample for the fluorescent or colored labels. Before moving on to the next imaging system, the first imaging system is erased. This is accomplished by contacting the sample with the first erasing molecule under conditions suitable for binding of the erasing molecule to either the first targeting arm or the first targeting molecule, which can be followed by washing away the first nanocage assembly.

Once that is complete the method can then involve contacting the sample with the second nanocage assembly under conditions suitable for binding of the targeting arm of the second DNA-cage assembly to the targeting molecule of the second targeting agent, followed by imaging the sample for the fluorescent or colored labels.

If a third imaging system is to be used, then the method can further involve contacting the sample with the second erasing molecule under conditions suitable for binding of the erasing molecule to either the second targeting arm or the second targeting molecule, which can be followed by washing away the second nanocage assembly. The above steps can then be repeated for any number of imaging systems so long as each has unique targeting molecules, targeting arms, and erasing molecules to avoid non-specific binding.

In other embodiments, the first and second (or more) imaging agents can be applied, imaged, and erased concurrently with each other. In this embodiment, multiple agents are imaged simultaneously and then erased to enable additional imaging cycles, thereby increasing the throughput of multiplexed labeling.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows FFPE sections stained with DAPI (nuclei), anti-PTBP1, and secondary antibody. FIG. 1B shows control sections stained with DAPI and secondary antibody only. In FIG. 1A, the PTBP1 signal present in nuclei (A2, white arrows) is weaker than background autofluorescence. Further, FIG. 1B shows a section of secondary control with significant hemorrhage. The red channel fluorescent image (B3) represents erythrocyte bleed through. Also, note the lack of background signal in the DAPI channel (A1 and B1) compared to the label (A2).

DETAILED DESCRIPTION

Figure 1:
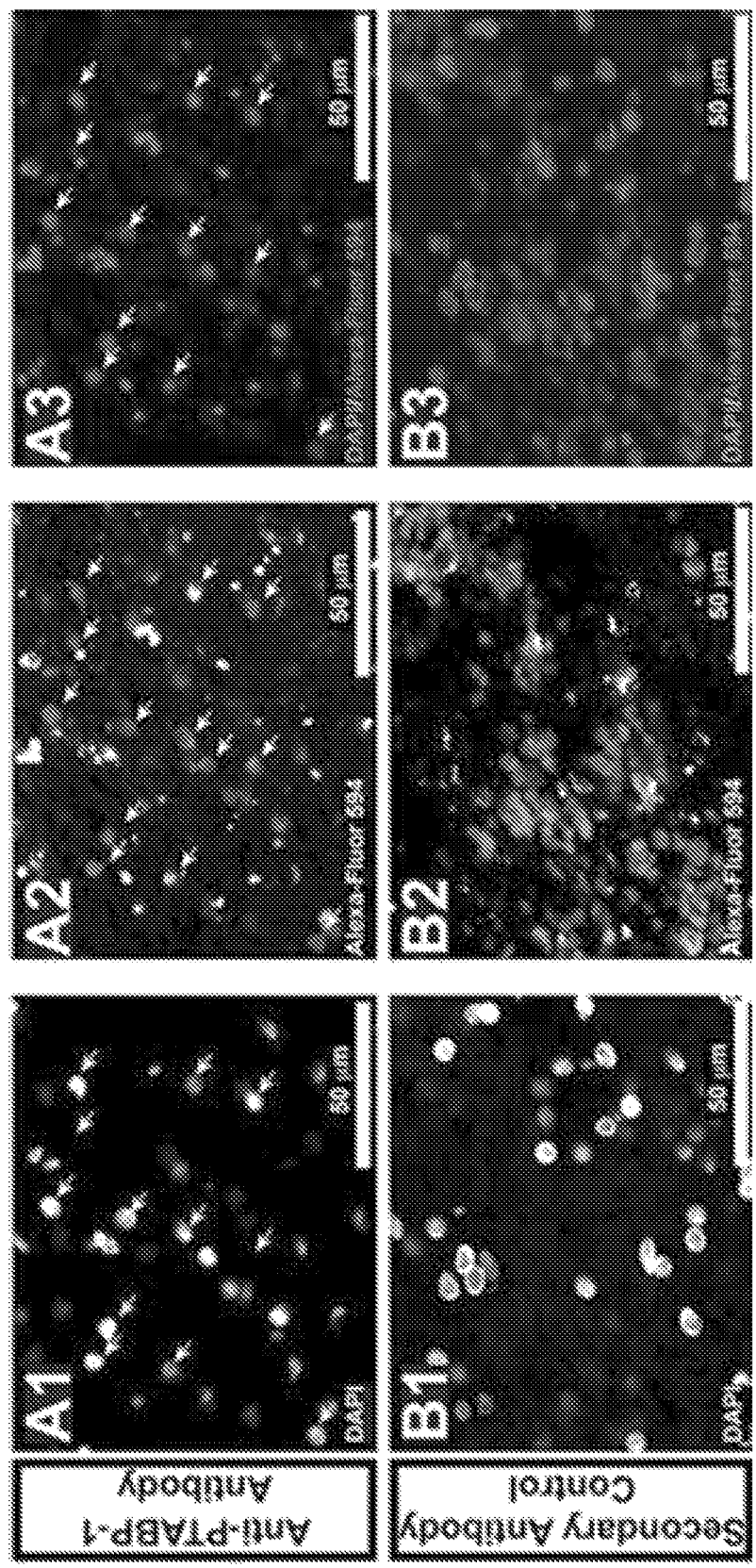
FIGS. 1A and 1B show challenges in immunofluorescent imaging of FFPE tissues.

The ability to quantitatively and spatially analyze multiple markers in tissue specimens would greatly enhance the utility of histological methods, complementing existing molecular biology techniques. Recognizing the need for multiplexed tissue analysis, automated, commercial multiplexing systems, such as MxIF (GE) [Gerdes, M. J., et al. Proc Natl Acad Sci USA. 2013 110(29):11982-11987] and the Imaging Cycler (ToposNomos) [EP0810428B1] have been developed. These systems employ fluorescent 'erasable' labels whose signals can be reduced via chemically-[Gerdes, M. J., et al. Proc Natl Acad Sci USA. 2013 110(29):11982-11987] or optically-[EP0810428B1] induced bleaching. This approach permits repeated inquiry of the same specimen, enabling multiple epitope retrieval methods to be employed and analysis of several biomarkers with a limited number of fluorophores. Despite their progress, these technologies have several limitations, including the requirement of specific fluorophores (e.g., MxIF requires dyes in the Cy family) [Gerdes, M. J., et al. Proc Natl Acad Sci USA. 2013 110(29):11982-11987] and efficiency loss with repeated cycles (i.e., 13% loss in fluorophore pairs) [Schubert, W., A. et al. Proc Natl Acad Sci USA 2014 111(2): E215-E215; Gerdes, M. J., et al. Proc Natl Acad Sci USA 2014 111(2):E216-E216]. Emerging research systems, such as Pelkmans 4i approach [Gut, G., et al. Science 2018 361(6401)], have addressed some challenges. However, these approaches have yet to be demonstrated in histological specimens or with immunohistochemistry (IHC) chromophores. Tissues present high background signals and could be damaged by the harsh conditions employed (e.g., guanidinium chloride, urea [Gut, G., et al. Science 2018 361(6401)], high light intensity, peroxide [Friedenberger, M., et al. Nature Protocols 2007 2(9):2285-94]). Thus, further improvements in erasable labels were needed to apply these approaches to histological specimens.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

Nanoparticles

Disclosed herein are nanoparticles loaded with or conjugated to imaging agents, such as fluorescent or colored molecules, that are encapsulated by DNA or RNA nanocages as disclosed herein. Agents can also be bound directly to DNA or RNA cages. For example, in some cases, the nanoparticles are made of amphiphilic polymers that self-assemble or aggregate. Other suitable nanoparticles include polylactic-co-glycolic acid, polystyrene, or silica nanoparticles. These nanoparticles are preferably hydrophilic on the surface and capable of being loaded with a hydrophobic imaging label. In certain embodiments, the nanoparticle could encapsulate hydrophilic labels in a hydrophilic core, e.g., liposomes, or in the interstitial space occupied by an aqueous phase, e.g., solid polymer or lipid nanoparticles.

In certain embodiments, the nanoparticles are amphiphilic nanoparticles encapsulating hydrophobic fluorescent or colored molecules (e.g. chromophores, fluorophores, or quantum dots (QDs)). The amphiphilic nanoparticles form by self-assembly of the amphiphile via standard methods in the field, including but not limited to, interfacial instability, solvent evaporation, water addition, and flash nanoprecipitation, when dispersed into an aqueous collection solution. In some embodiments, when the plurality of droplets enter into the aqueous solution, the amphiphiles spontaneously orient to form nanoparticles having a hydrophilic shell and a hydrophobic core. In some cases, during the nanoparticle formation, the hydrophobic fluorescent or colored molecules present are attracted to the hydrophobic segment of the amphiphile such that as the nanoparticles are self-assembling the hydrophobic fluorescent or colored molecules are drawn to and encapsulated within the hydrophobic core of the nanoparticle. In some embodiments, the hydrophobic molecules aggregate first and then the amphiphiles coat the surface of the aggregate to form a nanocomposite structure.

In this case, the core is defined by the aggregate size rather than the size of the hydrophobic blocks.

The size and shape of the resulting nanoparticles may be controlled by the amphiphile utilized. For example, poly (styrene-b-ethylene glycol) with molecular weight of 3800-b-6500 Dalton and 9500-b-18000 Dalton leads to MultiDots with diameters of 25 nm and 40 nm, respectively. Other amphiphiles, such as DSPE (distearoyl phosphatidyletha-nolamine)-co-polyethylene glycol (PEG) 2,000 form nanoparticles having a diameter of 15 nm with a core diameter of 6.5 nm. Thus, when engineering nanoparticles for specific applications requiring a particular size of particles, the size of the nanoparticles can be controlled by selecting an appropriate amphiphile. Moreover, amphiphilic block copolymers are particularly advantageous because these materials generally have a relatively long hydrophobic segment. The longer hydrophobic segment allows for the formation of amphiphilic nanoparticles having a larger hydrophobic core so that multiple and diverse types of hydrophobic fluorescent or colored molecules can be encapsulated within the nanoparticle, while at the same time remaining small enough (<100 nm) to be particularly useful in various diverse applications.

In some exemplary embodiments, the hydrophobic fluorescent or colored molecule is a quantum dot. Therefore, the disclosed nanoparticles can comprise a first quantum dot having a first emission wavelength. In some embodiments, each nanoparticle comprises a plurality of quantum dots having the same emission wavelength. In these embodiments, the brightness of the fluorescence emission is increased.

Example of the compositions and methods for making nanoparticles loaded with hydrophobic fluorescent quantum dots (referred to herein as "MultiDots") are disclosed in U.S. Pat. No. 9,550,160, which is incorporated by reference for these teachings.

As used herein, the term "quantum dots" refers to semiconductor nanocrystals having unique optical properties such as broad excitation spectra, narrow emission bandwidths, and enhanced photostability. Quantum dots generally have a diameter of about 2 nm to about 10 nm.

In some cases, a combination of quantum dots are used. For example, a first nanoparticle can be loaded with a first quantum dot, and a second nanoparticle can be loaded with a second quantum dot. If the first and second quantum dots have distinct emission wavelengths, then the first and second nanoparticles with different targeting agents can be used simultaneously. In some exemplary embodiments, at least one first quantum dot has a first emission wavelength between 490 nm to 560 nm and the at least one second quantum dot has a second emission wavelength between 590 nm to 700 nm. Various other combinations of quantum dots having different emission wavelengths (i.e., colors) may be utilized. For example, the emission wavelengths may range from about 380 nm to about 800 nm, also including infrared. In certain embodiments, the first emission wavelength may be about 380 nm to 450 nm, or about 450 nm to about 495 nm, or about 495 nm to about 570 nm, or about 570 nm to about 590 nm, or about 590 nm to about 620 nm, or about 620 nm to about 750 nm, and the second emission wavelength may be within any one of the aforementioned ranges that is not the same range as the first emission wavelength. By providing a second emission wavelength that is different from the first emission wavelength the colors emitted by the quantum dots encapsulated within the nanoparticles are able to be distinguished.

A wide variety of amphiphiles may be used to produce nanoparticles. The term "amphiphile," as used herein, refers to a chemical compound that includes a hydrophilic segment and a hydrophobic segment. In certain embodiments, the amphiphile is an amphiphilic block copolymer. In certain other embodiments, the amphiphile is a peptide amphiphile. Other amphiphiles include lipid-polymers, lipids, and surfactants. It is also possible for random polymers, star polymers, dendrimers, and polymers with more than two blocks (e.g., tri-block copolymers) to be employed. Suitable amphiphilic block copolymers include, but are not limited to, poly(styrene-b-ethylene glycol), poly(ε-caprolactone-b-ethylene glycol), poly(ethylene glycol-b-distearoyl phophatidylethanolamine), and combinations thereof. Suitable peptide amphiphiles include, but are not limited to, palmitoyl-VVAAEE-$NH_2$, palmitoyl-VVAAEEGIKVAV-COOH, palmitoyl-VVAAEEEEGIKVAV-COOH, and combinations thereof. Those of skill in the art will appreciate that various other amphiphiles may be utilized and are within the scope of the general inventive concepts contemplated herein.

In some exemplary embodiments, MultiDots have an average diameter in a range of about 5 nm to about 1000 nm. In another exemplary embodiment, the MultiDots have an average diameter in a range of about 10 nm to about 800 nm, including about 20 nm to about 700 nm, including about 25 nm to about 500 nm, including about 30 nm to about 100 nm, including about 30 nm to about 70 nm, and also including about 30 nm to about 50 nm.

Nanocages

Disclosed herein are DNA or RNA oligonucleotides that self-assemble into oligomers with sticky ends, which then allow the oligomers to interconnect as a DNA or RNA nanocage around a nanoparticle. In some embodiments, the nanocage is produced essentially as described in Kurokawa, C., K. et al. Proc Natl Acad Sci USA 2017 114(28):7228-7233, which is incorporated by reference for these DNA nanocages, with the modification that the DNA nanocage also contains a ssDNA or ssRNA "targeting arm" as described herein. However, in contrast to Kurokawa, et al., the disclosed nanoparticles are encapsulated by the DNA nanocage instead of the nanocage forming a cytoskeleton inside the nanostructure.

Figure 2A:
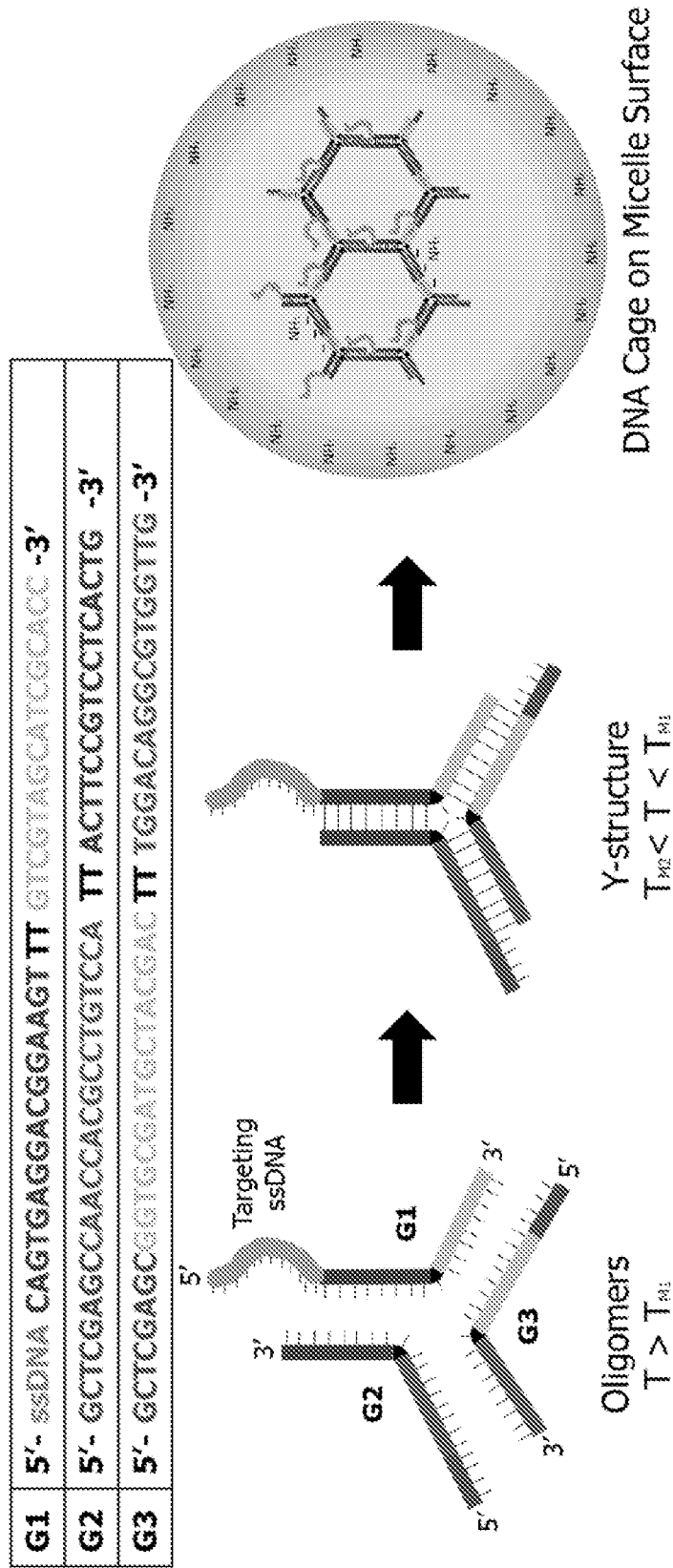
FIG. 2A shows one embodiment of the DNA-cage assembly. Interlocking ssDNAs form a cage surrounding the nanoparticle. Free ssDNAs are available for targeting via reversible DNA binding. Sequences shown are G1 (SEQ ID NO:1), G2 (SEQ ID NO:2), and G3 (SEQ ID NO:3).

Briefly, each of the oligomers can contain at least three ssDNA oligonucleotides that self-assemble into a Y-motif DNA having three arms (FIG. 2A). The following are example sequences for these oligonucleotides:

(SEQ ID NO: 1)
5'-ssDNA-CAGTGAGGACGGAAGT-TT-*GTCGTAGCATCGCACC*-3';

(SEQ ID NO: 2)
5'-GCTCGAGC-caaccacgcctgtcca-TT-ACTTCCGTCCTCACTG-3';

or (SEQ ID NO: 3)
5'-GCTCGAGC-*GGTGCGATGCTACGAC*-TT-tggacaggcgtggttg-3'.

In the above sequences, "ssDNA" represents an ssDNA targeting arm that can bind either a DNA or RNA target, or a single stranded oligonucleotide molecule of a targeting agent as described herein. The nucleic acid sequence GCTCGAGC represents a palindromic sticky end that will cohere to a sticky end on another oligomer. The two thymidines represent linkers between the complementary regions. It is understood that other suitable bases of various lengths could be used. The bolded sequences represent a first complementary pair, the italicized sequences represent a second complementary pair, and the lowercase sequences represent a third complementary pair.

In some cases, the length of the targeting arm can be from 6 to 40 bases in length, including 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases in length.

As shown in FIG. 2A, the ssDNA or ssRNA oligonucleotides first self-assemble into oligomers with sticky ends. These sticky ends then allow the oligomers to interconnect and form nanocages around a nanoparticle.

The disclosed nanocages contain at least one targeting arm. In some cases, the targeting arm has a nucleic acid sequence complementary to a DNA or RNA target. In other embodiments, the targeting arm has a nucleic acid sequence complementary to a single stranded oligonucleotide "targeting molecule" conjugated directly or indirectly to a targeting antibody as described below. The sequence of the targeting molecule can be selected and designed using routine methods to provide optimal specificity without non-specific binding. For example the caDNAno program can be used to design complementary sequences.

Additional compositions and methods for producing DNA and RNA nanocages are known in the art, and are described, for example, in U.S. 2005/0112578, which is incorporated by reference for these teachings. Generally, oligonucleotide strands for use in producing the disclosed oligomers and nanocages can be synthesized with an automatic synthesizer or the like using a phosphoroamidite method.

It is preferable that the process for producing DNA and RNA nanocages is performed at a temperature lower than a temperature at which double-strand DNAs are dissociated (melting temperature). The melting temperature depends on the sequences of the oligonucleotides.

The length of the ssDNA or ssRNA oligonucleotides used to produce the nanocage is preferably from approximately 10-mer to 100-mer. The lengths of the at least three ssDNA oligonucleotides may be the same or different from one another. When the lengths are the same, oligomers with high symmetry are obtained, which is preferable to form spherical cages. It is also possible to construct an asymmetrical structure using different lengths.

In the process for producing the nanocages, the total concentration of the ssDNA or ssRNA oligonucleotides can be 1 µM or more. In addition, the salinity of the aqueous solutions can be from 0.25 M to 1.0 M, including approximately 0.5 M.

The disclosed nanocages are cage-shaped assemblies forming polygonal, e.g. spherical, structures. The diameter of nanocages is dependent on the diameter of the nanoparticle it encapsulates.

Targeting Agents

As noted above, in some cases the targeting arm is itself a targeting agent that binds a DNA or RNA target. However, in other embodiments, the disclosed system can also contain one or more targeting agents, such as antibodies or aptamers, that are directly or indirectly conjugated to a single stranded oligonucleotide that is at least partially complementary to the targeting arm.

The length of the single stranded oligonucleotide "targeting molecule" can be from 6 to 35 bases in length, including 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases in length. The sequence of the targeting molecule can be selected and designed using routine methods to provide optimal specificity without non-specific binding. As discussed below, the affinity of the targeting molecule for the targeting arm should be high enough to provide selective binding; however, the erasing molecule preferably has a higher binding affinity for either the targeting molecule or the targeting arm in order to force dissociation of the nanoparticles from the target or targeting agent. Binding affinity of oligonucleotides is a function of length, complementarity, and GC content. These and other parameters can therefore be used to design suitable ssDNA or ssRNA molecules.

In some embodiments, the system comprises a plurality of targeting antibodies that bind different targets. It is understood that each of these targeting antibodies will have a unique targeting molecules matched to the targeting arms and corresponding nanoparticles.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Erasing Molecule

The disclosed system also involves ssDNA or ssRNA "erasing molecules" that can induce dissociation of bound nanoparticles from targets or targeting agents so that the nanoparticles can be washed away. The erasing molecule can have a nucleic acid sequence that is complementary to either the targeting arm of the nanocage or the targeting molecule. The erasing molecules can be from 6 to 50 bases in length, including 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases in length. The sequence of the erasing molecule can be selected and designed using routine methods to provide optimal specificity and affinity without non-specific binding. As discussed above, the erasing molecule preferably has a higher binding affinity for either the targeting arm or the targeting molecule than they do for each other in order to force dissociation of the nanoparticles from the target or targeting agent.

Each of the oligonucleotides, e.g., ssDNA or ssRNA molecules, described herein can contain either natural or synthetic polynucleotides. For example, compositions and methods for increasing stability of nucleic acid half-life and nuclease resistance are known in the art, and can include one or more modifications or substitutions to the nucleobases, sugars, or linkages of the polynucleotide. For example, the polynucleotide can be custom synthesized to contain properties that are tailored to fit a desired use. Common modifications include, but are not limited to use of locked nucleic acids, unlocked nucleic acids (UNA's), morpholinos, peptide nucleic acids (PNA), phosphorothioate linkages, phosphonoacetate, linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In one embodiment, the polynucleotide includes internucleotide linkage modifications such as phosphate analogs having achiral and uncharged intersubunit linkages (e.g., Sterchak, E. P. et al., Organic Chem., 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Locked nucleic acids (LNA) are modified RNA nucleotides (see, for example, Braasch, et al., Chem. Biol., 8(1):1-7 (2001)). Commercial nucleic acid synthesizers and standard phosphoramidite chemistry are used to make LNAs. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD). The latter methods avoid the problem of elemental sulfur's insolubility in most organic solvents and the toxicity of carbon disulfide. The TETD and BDTD methods also yield higher purity phosphorothioates. (See generally Uhlmann and Peymann, 1990, Chemical Reviews 90, at pages 545-561 and references cited therein, Padmapriya and Agrawal, 1993, Bioorg. & Med. Chem. Lett. 3, 761).

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

In some embodiments, the polynucleotide includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-fluoro (2'-F) pyrimidines appear to have favorable properties in vitro (Chiu and Rana 2003; Harborth et al. 2003). Moreover, one report recently suggested 2'-F modified siRNAs have enhanced activity in cell culture as compared to 2'-OH containing siRNAs (Chiu and Rana 2003). 2'-F modified siRNAs are functional in mice but that they do not necessarily have enhanced intracellular activity over 2'-OH siRNAs.

In some embodiments the polynucleotide includes one or more sugar moiety modifications, including, but not limited to, 2'-O-aminoethoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Erasable Label Technology in Solution

DNA cages were assembled on particle surfaces using state of the art chemical engineering methods that enable release from targets by reversible DNA binding. Particles offer the flexibility to encapsulate a wide variety of reporter compounds, while maintaining consistent surface properties, reducing the need for label-by-label chemistry optimization. The use of DNA cages amplifies signal compared to competing single-stranded (ss) DNA duplex labels [Duose, D. Y., et al. Bioconjugate Chemistry 2010 21(12):2327-31; Agasti, S. S., et al. Chemical science 2017 8(4):3080-3091], and also offers multiple ssDNA binding sites. RNA could also be used. Labels are erased through biologically-friendly, reversible, complementary binding interactions between ssDNA strands extending from the DNA-cage. The proposed advances in labeling are based on innovations in encapsulation using polymer particles, micelles, and other nano- or micro-particles (e.g., silica) and DNA nanotechnology.

Figure 3A:
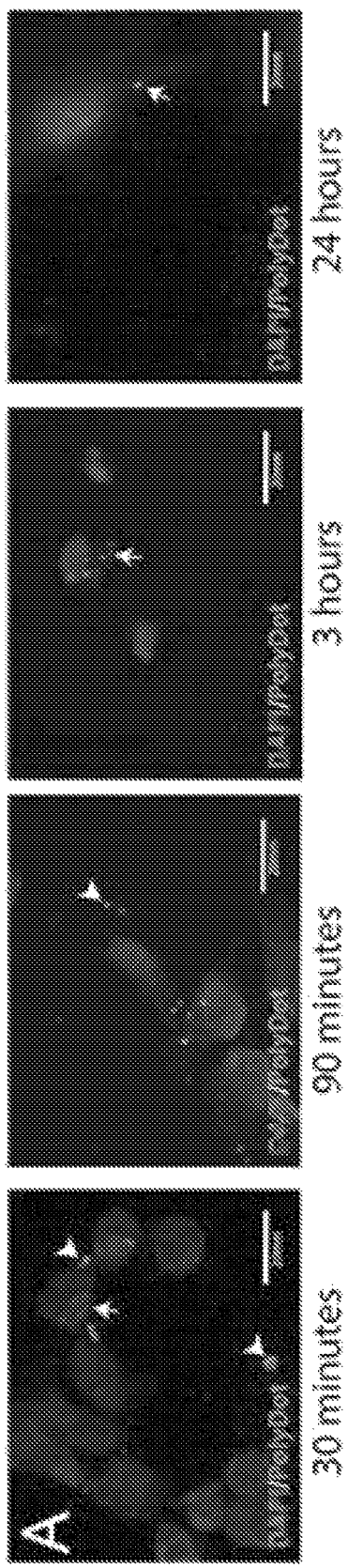
FIGS. 3A and 3B shows green coumarin-6 PolyDot nanoparticles that can be used for intracellular trafficking (FIG. 3A, arrows) or in vivo biodistribution studies (e.g., accumulation in mouse brain (FIG. 3B, white)). These nanoparticles are suitable supports for DNA cage assembly.
Figure 3B:
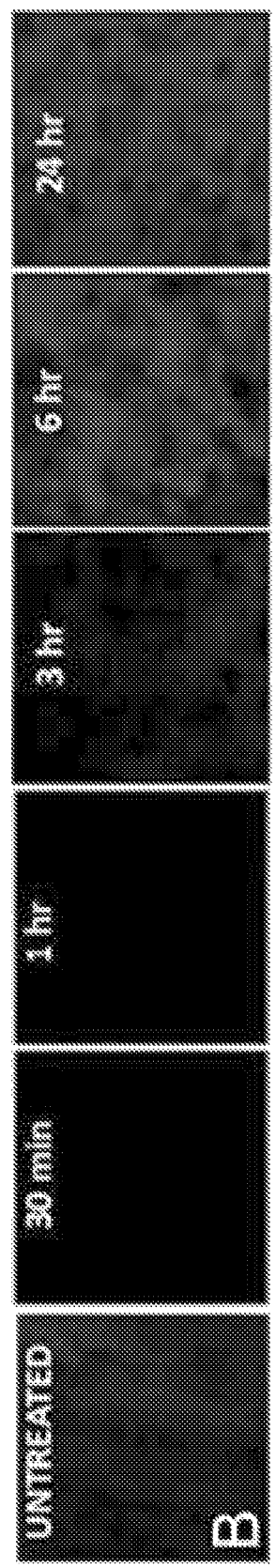
Figures 4A, 4B, 4C:
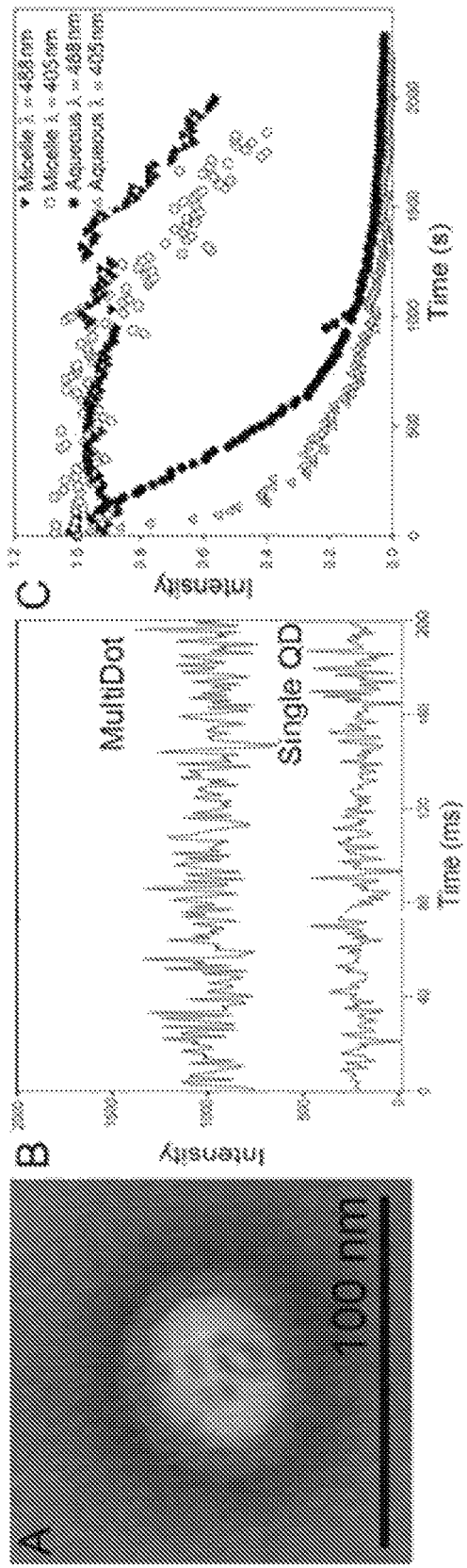
FIG. 4A shows ~30-40 nm MultiDot nanoparticles encapsulating QDs (FIG. 4A, TEM) are 4-13× brighter than single QDs (FIG. 4B) with increased resistance to photobleaching (FIG. 4C). These nanoparticles are suitable supports for DNA cage assembly.

Particle Labeling Platforms: We have developed a range of labeling technologies based on polymer encapsulation of dyes [Nabar, G. M., et al. Inter J Nanomed 2018 13:351-366] and quantum dots [Ruan, G. et al. Nano Letters 2011 11(3):941-945]. However, any particle encapsulating, conjugated to, containing or coated with a fluorophore, QD, or chromophore could be employed. Using poly(styrene)-b-poly(ethylene oxide) (PS-b-PEO) block co-polymers and 1,2-distearoyl-sn-glycero-3-phosphoethanolamine-N-poly (ethylene glycol) (DSPE-PEG) lipid-polymers, 10-50 nm polymer nanoparticle labels were created that encapsulate coumarin-6 fluorophores (FIG. 3) or quantum dots (QDs) (FIG. 4). These labels have been used for intracellular tracking and pharmacokinetic studies in vitro and in vivo (FIG. 3), demonstrating label ability to permeate cells and tissue.

For example, polymer nanoparticles containing fluorophore (e.g., 4-Bromomethyl-7-methoxycoumarin; 4-Bromomethyl-6,7-dimethoxy-coumarin; 7,8-Dihydroxy-4-methylcoumarin; or coumarin-6), chromophore (e.g., Indigo, Quinizarin), or QDs (e.g., CdS/ZnS, CdSe/ZnS) are synthesized as described previously [Nabar, G. M., et al. Inter J Nanomed 2018 13:351-366; Duong, A. D., et al. Langmuir 2014 30(14):3939-3948]. For example, PS-b-PEO is added to tetrahydrofuran (THF) (5 mg/ml) and electrosprayed at a voltage of −2500 V directly into distilled water (10 ml), i.e. without air exposure, at a rate of 12.7 ml/hr to a total volume of 0.2 ml polymer.

Figures 5A, 5B:
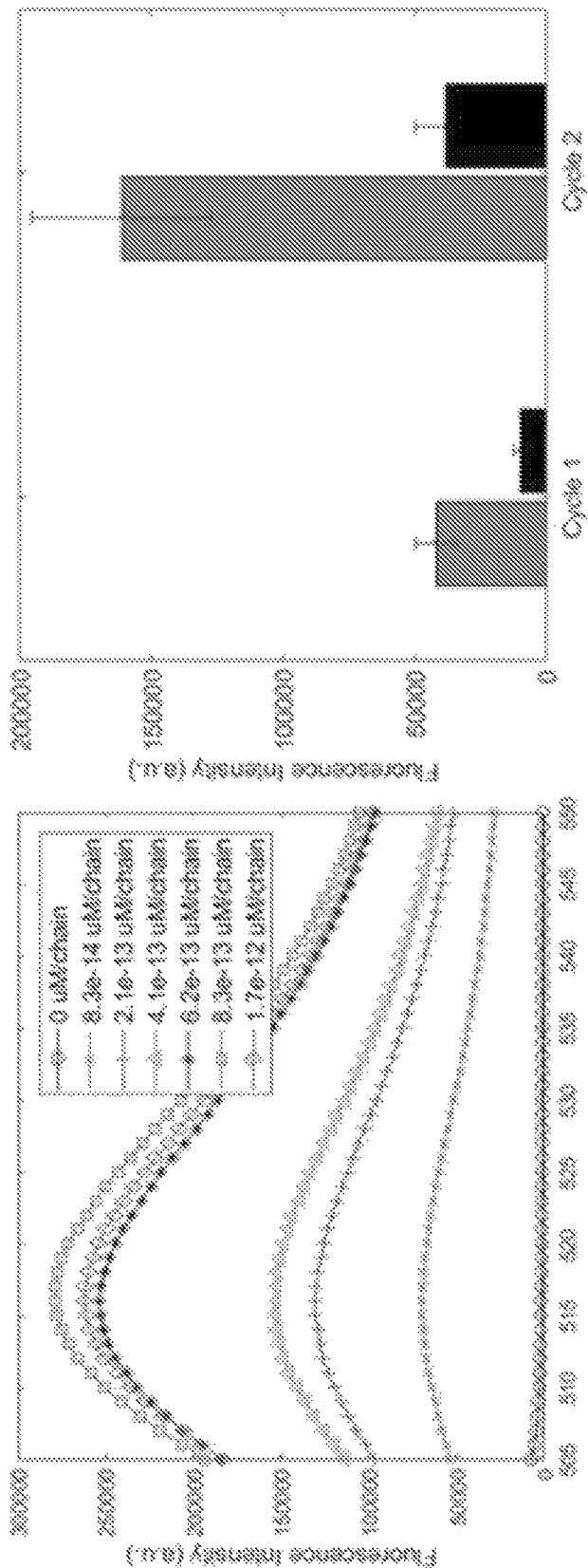
FIG. 5A shows DNA-cage formation as a function of fluorescent DNA tile concentration. Nanoparticles are saturated at ~6E-13 μM DNA/polymer chain (black).
FIG. 5B shows erasability in solution. DNA-caged nanoparticles with a targeting sequence of 5'-AAAAATTTCGACGTTA-CATGCACC TC-3' (SEQ ID NO:5) were exposed to complementary DNA bound to fluorescent Cy 5 (gray bars). With introduction of longer complementary DNA sequences, the dye tagged strand was removed (black bars. Erase efficiency=76%±10% in cycle 1 and 81%±3% in cycle 2 as a result of increasing ssDNA complementarity with the erase strand.
Figure 7A:
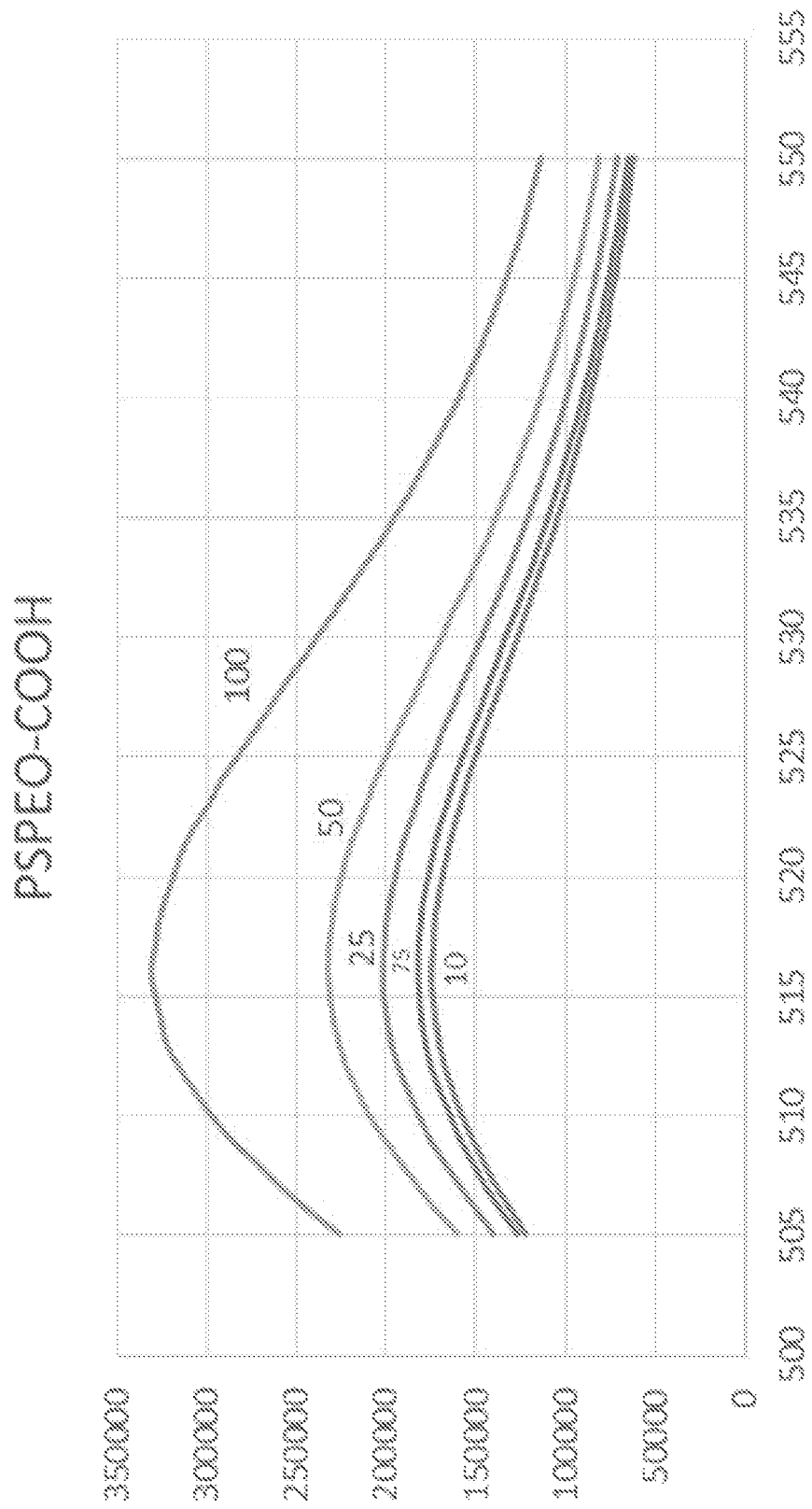
FIGS. 7A to 7C show saturation curves for attachment of DNA cages to polystyrene-b-polyethylene oxide (PSPEO) polymer nanoparticles terminated in both —$NH_2$ (FIG. 7B) and —COOH (FIG. 7A) groups, as well as 1,2-distearoyl-sn-glycero-3-phosphoethanolamine-N-[amino(polyethylene glycol)] (DSPE-PEG) (FIG. 7C) polymer nanoparticles. y axis: fluorescence intensity in arbitrary units (a.u.). x axis: fluorescence wavelength in nm. Values in the legend are the volume ratio of DNA tiles in solution to nanoparticles in water. DNA tiles were assembled on nanoparticle surfaces using fluorescent DNA. Thus, as additional tiles are added, fluorescence increases. At a certain point, the surface is saturated and additional increases are no longer seen. Signal may also decline after saturation as DNA cage formation in solution is favored over nanoparticle surface adsorption. All nanoparticles employed yielded cage formation regardless of surface charge (—COOH negative charge or —$NH_2$ positive charge).
Figure 7B:
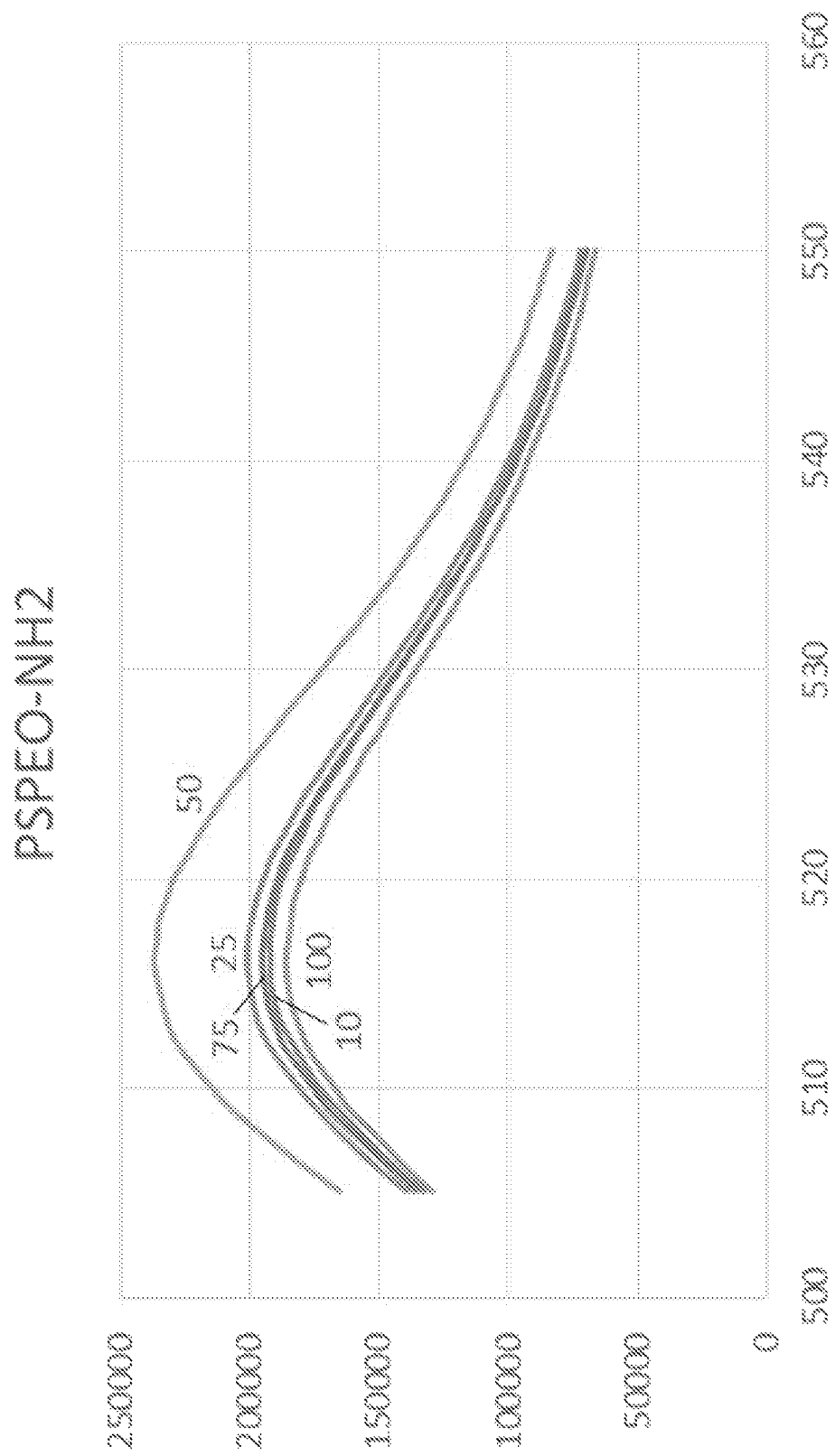
Figure 7C:
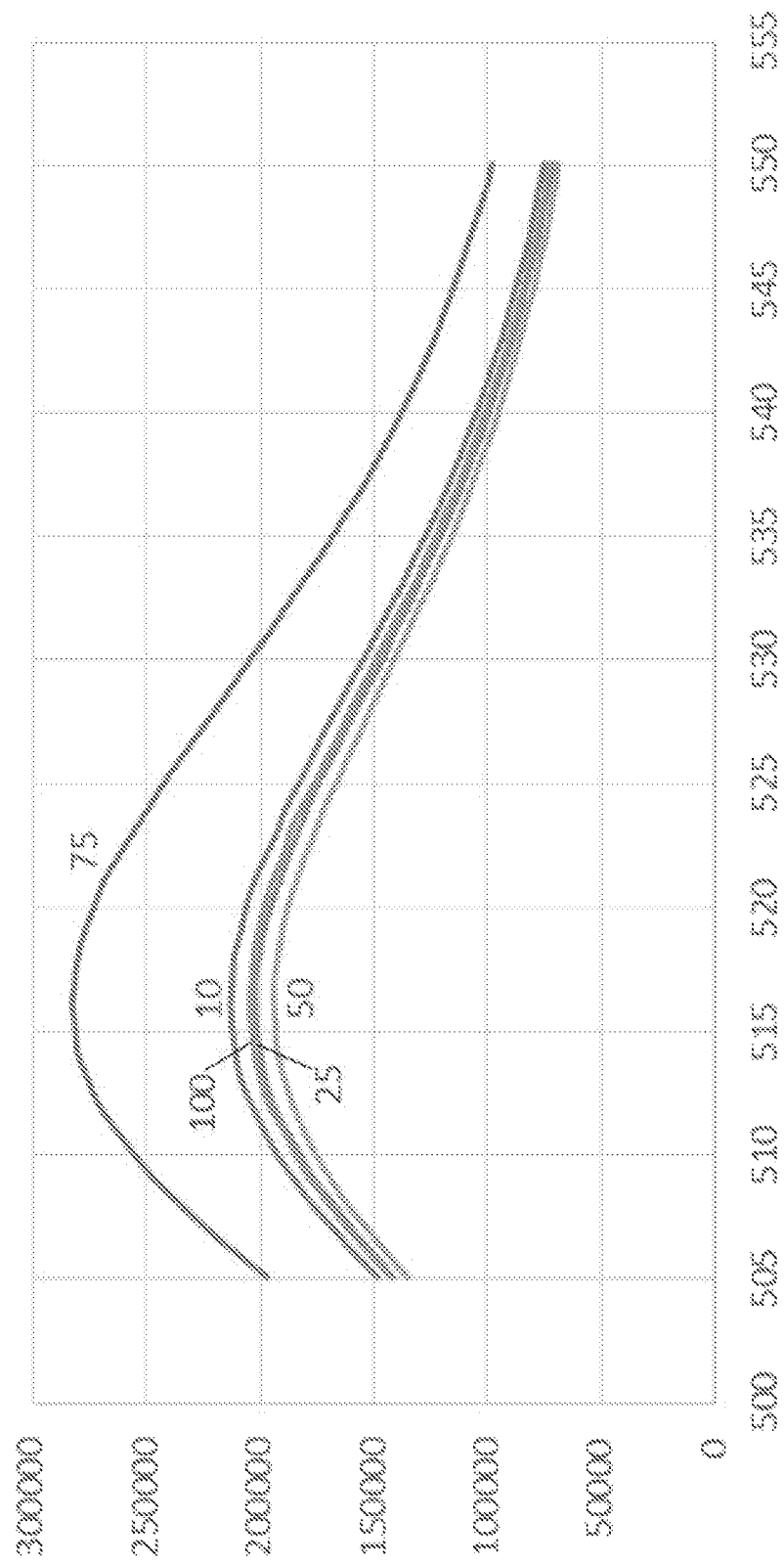
Figure 8:
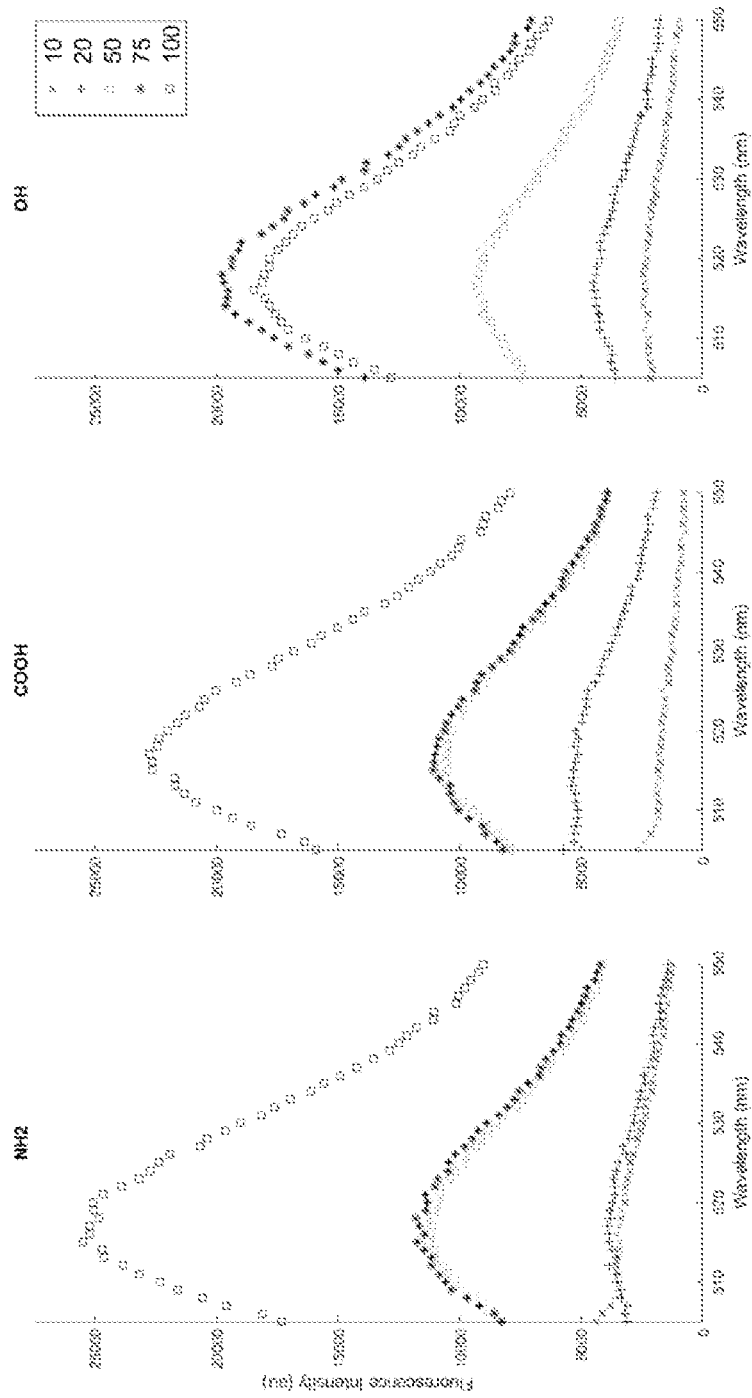
FIG. 8 shows saturation curves for attachment of DNA cages to polystyrene nanoparticles terminated in —$NH_2$, —COOH, and —OH groups. Values in the legend are the volume ratio of DNA tiles in solution to nanoparticles in water. DNA tiles were assembled on nanoparticle surfaces using fluorescent DNA. Thus, as additional tiles are added, fluorescence increases. At a certain point, the surface is saturated and additional increases are no longer seen. Signal may also decline after saturation as DNA cage formation in solution is favored over nanoparticle adsorption. All nanoparticles employed yielded cage formation regardless of surface charge (—COOH negative charge, —$NH_2$ positive charge, or —OH uncharged).

DNA Nanostructures: Particles can be modified with DNA (or RNA) tile-based cages that enable reversible binding (FIG. 5A, 5B). Adapting the method of Kurokawa et al. [Kurokawa, C., K. et al. Proc Natl Acad Sci USA 2017 114(28):7228-7233], who used similar DNA structures to form artificial cytoskeleton networks inside liposomes, nanoparticle surfaces were modified with triangular, interlocking DNA tiles (FIG. 5A). In that report, Kurokawa instructs that negatively-charged DNA tiles (Y structure in FIG. 2A) are attracted to positively-charged $NH_2$-terminated nanoparticles, where they self-assemble into cages via interactions between interlocking sequences (FIG. 2A). However, we have discovered that DNA cages bind to polymer surfaces regardless of surface charge, which is not obvious to one trained in the state of art by Kurokawa (FIGS. 7A to 7C). Successful cage formation has been observed for polystyrene-b-polyethylene oxide (PSPEO) polymer nanoparticles terminated in both —$NH_2$ and —COOH groups, as well as 1,2-distearoyl-sn-glycero-3-phosphoethanolamine-N-[amino(polyethylene glycol)] (DSPE-PEG) polymers terminated with —$NH_2$ groups. Cage formation has also been observed on the surface of polystyrene nanoparticles terminated with —NH2, —COOH, and —OH (FIG. 8).

Figure 2B:
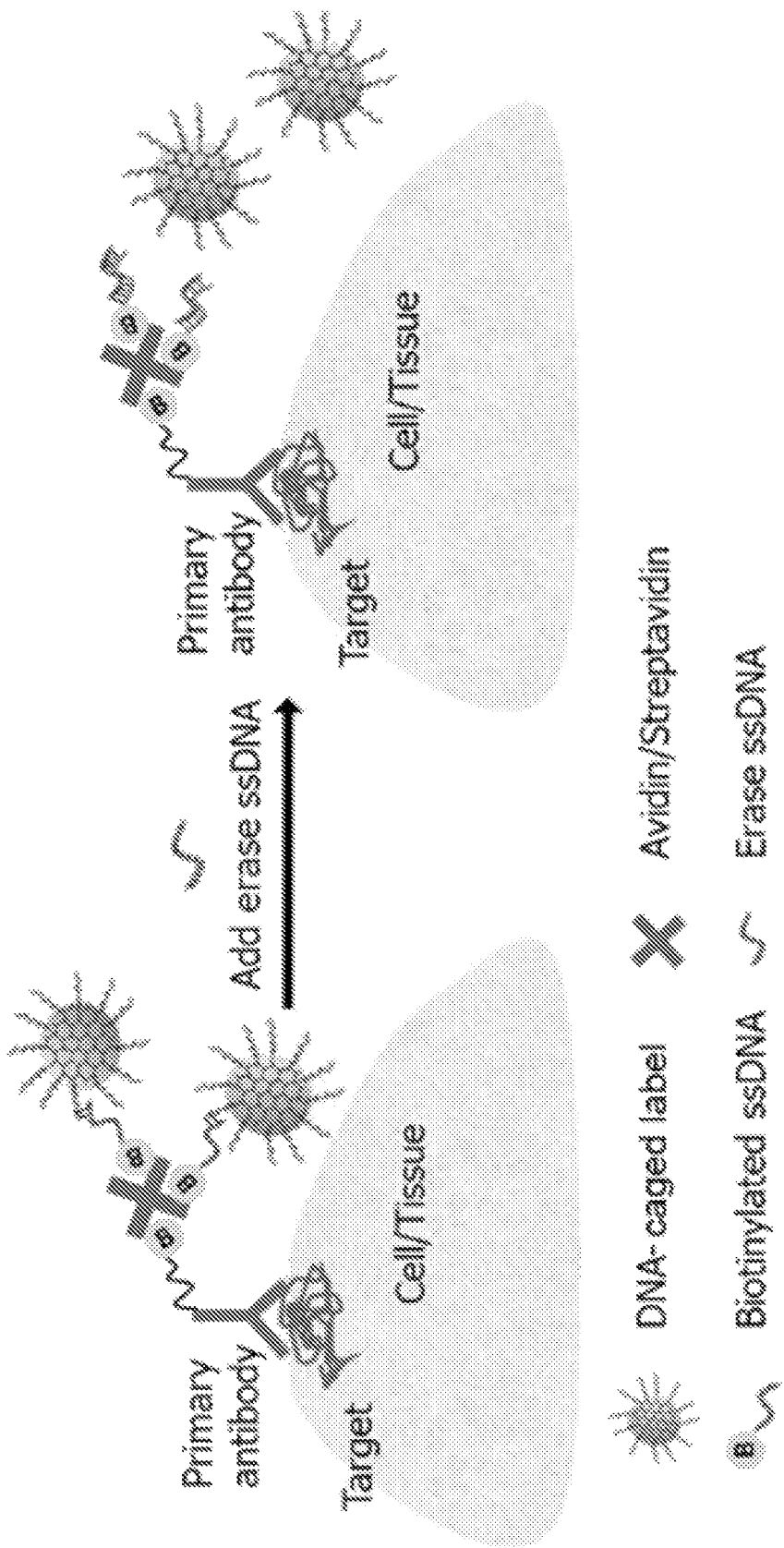
FIG. 2B shows an example of indirect erasable labeling. DNA-cages are attached to biotinylated antibodies using complementary ssDNA modified with biotin. Antibodies are linked to DNA cage ssDNA through biotinylated ssDNA linker molecules and streptavidin molecules. Erase occurs when ssDNA sequences with higher complementary are added. Biotinylated primary antibodies targeting antigens on the cell surface are added. Alternatively, unmodified primary antibodies can be employed with a biotinylated secondary. Then, streptavidin (purple) is used to bind the antibody. DNA cages are biotinylated by addition of biotinylated ssDNA complementary to the ssDNA targeting sequence on the DNA cage. Biotinylated cages can then bind to the streptavidin. To erase DNA cages, ssDNA with increased complementarity to the ssDNA cage targeting strand is added (orange).
Figure 2C:
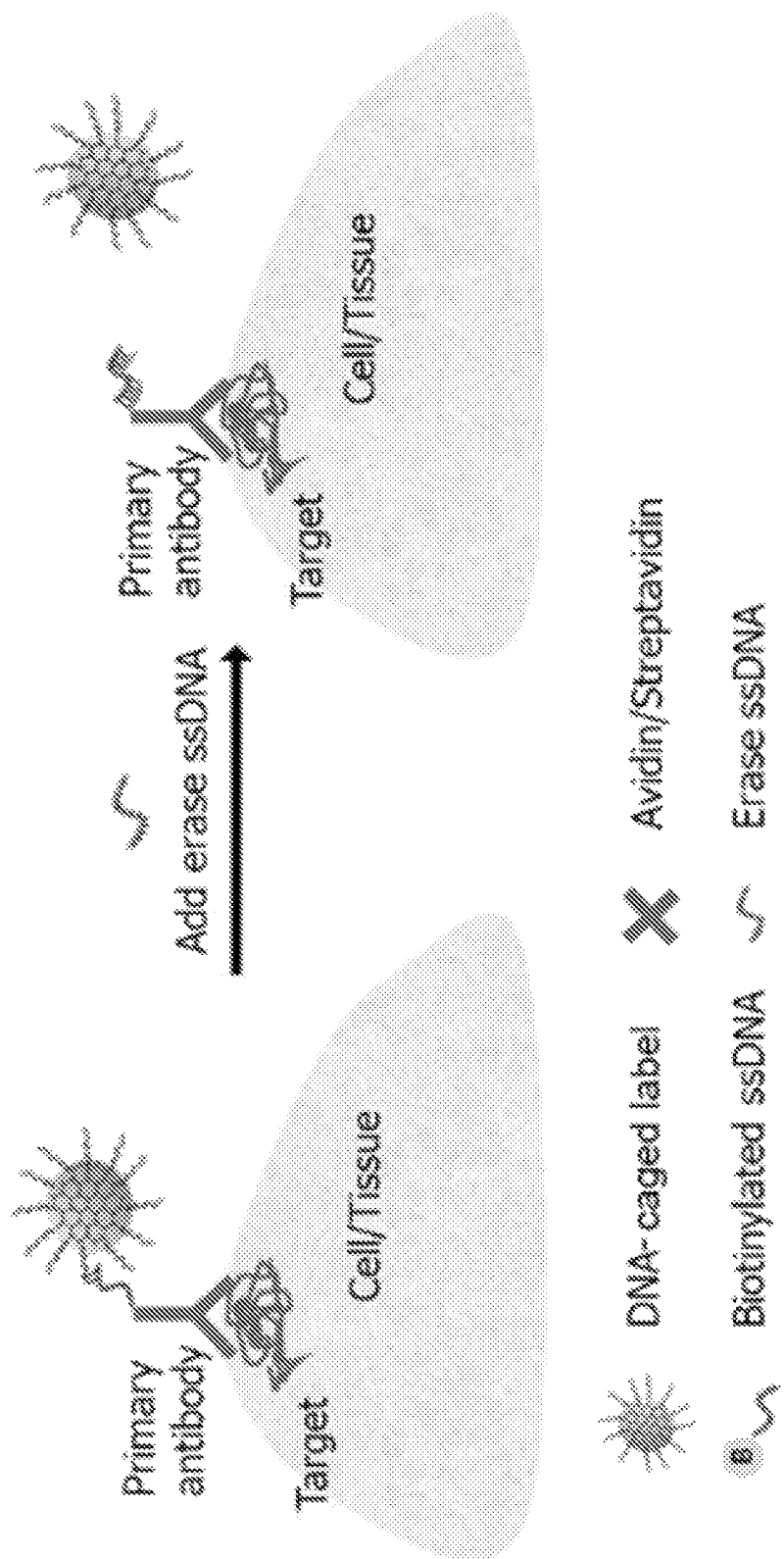
FIG. 2C shows an example of direct erasable labeling where ssDNA can be directly conjugated to the antibodies (primary or secondary) with no need for avidin or biotin in the system.
Figure 6:
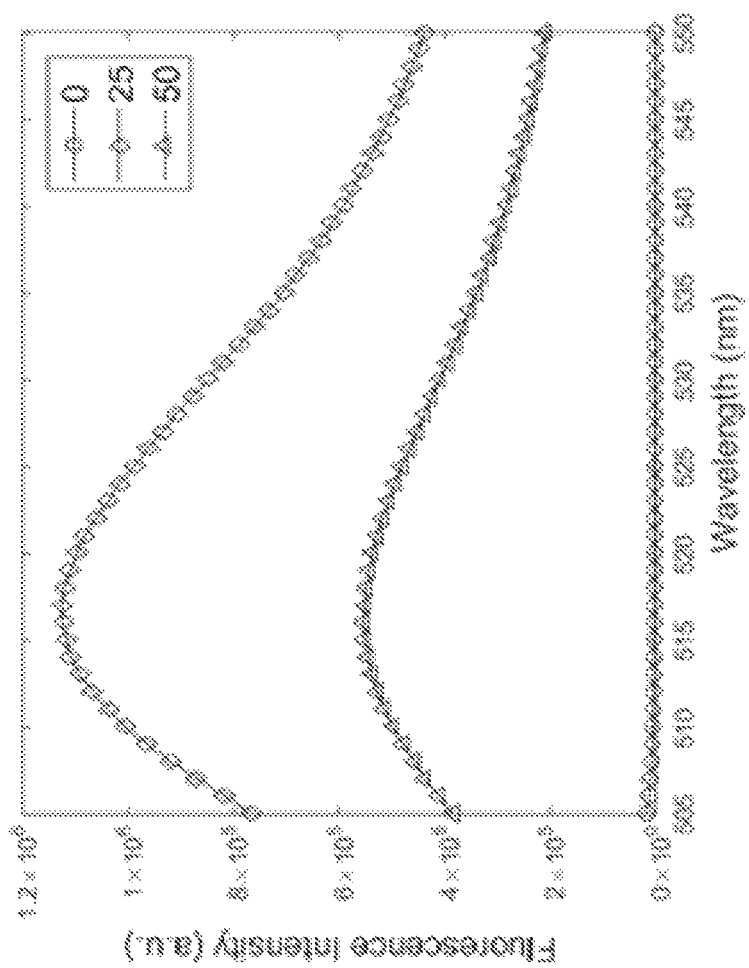
FIG. 6 shows DNA-cage formation observed via fluorescence quenching between interlocking ssDNA strands. Initially signal increases (0 to 25 DNA: tile by vol.) as tiles absorb to nanoparticles; signal quenches as more sequences are added (25 to 50) and interlock.

Specifically, DNA tiles are assembled using the sequences shown in FIG. 2 (i.e., G1-G3). To enable targeting, 1/120th (by vol.) of G1 interlocking sequences are replaced with targeting ssDNA as described above (9-30 bps). In selected samples, an additional 1/120th of G1 and G2 sequences is modified with FAM-6 ($\lambda$ex/em=495/515 nm) and black hole quencher, respectively, to observe cage formation via dye quenching (FIG. 6). Each DNA sequence is dissolved in 20 mM Tris-HCl and 350 mM NaCl at 18 μM, mixed in equal volume, and heated at 80° C. for 10 minutes. Tile solutions are then cooled and stored at 4° C. until used.

Next, nanoparticles containing reporter molecules (5 μL in water) and DNA tiles (500 μL in buffer) are mixed and incubated at room temperature for 10 minutes. The resulting DNA-caged particles are purified via microcentrifugal filtration (100 kDa cut off) at 14000 rpm for 3 minutes and washed 3× with 500 μl dl water.

DNA Cage Targeting: Biomarker targets are identified using ssDNA targeting sequences (FIG. 2A), which can be any D/RNA sequence between approximately 6-35 base pairs (bps). This approach permits facile identification of nucleic acid targets through complementary binding. To evaluate proteins, such as antigen targets, ssDNA sequences can be bound to biotinylated complement DNA and avidin/biotinylated antibodies. This approach employs pre-existing reagents, enabling low adoption costs by the life sciences community. Alternatively, primary antibodies can be directly modified with ssDNA complementary to the ssDNA targeting sequence.

DNA Erase Procedures: Next, the principle of erasable labeling in the solution phase was demonstrated. For these experiments, DNA-caged labels were bound to a fluorescent ssDNA strand that was targeted by the complementary ssDNA targeting strand on the cage (FIG. 2A). When the fluorescent ssDNA binds the cage, the signal goes up. This strand is erased by adding ssDNA of increasing complementary to the ssDNA targeting sequence. This displaces the fluorescent ssDNA, reducing the signal. In these experiments, the repeatability of erase was demonstrated by performing 2 label/erase cycles using strands that were successively 9, 12, 15, and 27 base pairs long. Using this approach, there was an erasability of ~ 80% over repeated cycles (76%±10% cycle 1; 81%±3% cycle 2) with increasing erase percent as ssDNA erase length increased (e.g., 9/12 bp cycle 1 vs. 15/26 bp cycle 2) (FIG. 5B).

Example 2: Erasable Label Technology for Cell Labeling

Next-generation 'erasable' labels (FIG. 2A) were developed that involve small reporter molecules (chromophores, fluorophores, or quantum dots (QDs)) in polymeric carriers. Here, erasable labeling of cells was demonstrated using DNA-cage labels. This generates labels compatible with standard IHC procedures (chromophores for brightfield microscopy) and research applications (QDs for fluorescent microscopy). DNA-caged nanoparticles are assembled as described in Example 1 using PSPEO polymers and coumarin-6 encapsulants.

Cell Labeling: Two possible approaches are employed for antigen labeling. Indirect Avidin-Biotin Approach: In the first approach, avidin-biotin coupling is used to indirectly label targets. Briefly, biotinylated ssDNA complementary to targeting ssDNA (e.g., biotin-GAT TAT CAA AGA GGT GCA TGT AAC GTCG, SEQ ID NO:4) is added (10 μL) to 100 μL of 360 μM DNA cages and incubated for 15 min. The solution is purified via centrifugal filtration and diluted to 100 μL to generate biotinylated-DNA-cage labels. Standard primary/secondary avidin-biotin labeling procedures are then employed to label targets. Briefly, streptavidin is added at 10:1 or 20:1 to generate streptavidin-biotin-DNA-cage conjugates. These are employed at standard concentrations with the secondary antibody. To reduce cross talk between antibodies, each complete complex is generated separately (label, biotinylated ssDNA, avidin, biotinylated secondary antibody) prior to cell labeling.

Direct ssDNA conjugation Approach: Also used are methods in which ssDNA complementary to the targeting sequence is directly conjugated to primary antibodies. Purified antibodies are conjugated to amine-terminated ssDNA sequences using Sulfo-NHS (N-hydroxysulfosuccinimide) assisted carbodiimide (EDC) chemistry. Briefly, carboxylic acid groups of antibodies are activated by mixing with EDC (COOH:EDC~1:400) and sulfo-NHS in MES buffer (0.1 M, pH 5) for 15 minutes. Activated antibodies are exchanged to phosphate buffered saline (PBS) buffer (0.1 M, pH 7.2), reacted with amine-ssDNA (1:30 DNA) for 4 hr, and purified using size exclusion chromatography.

Figure 5C:
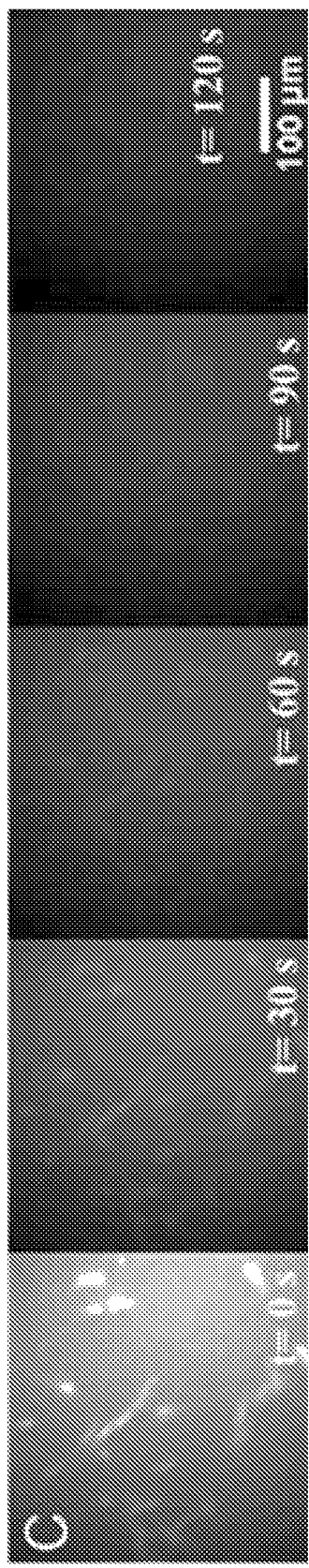
FIG. 5C shows fibroblast P1 integrins labeled using 6-FAM tagged DNA-caged nanoparticles and erased with longer complementary ssDNA strands.

Erase Procedure: Cells are washed (e.g., to remove antifade). Then, DNA-cage labels are erased by adding ssDNA with increased complementarity (e.g., +1-3 bps compared to DNA-cage targeting ssDNA as in FIG. 5C) (18 μM in 20 mM Trizma base with 350 mM NaCl) and incubating for ~15 minutes. Exact incubation times are determined using time lapse video microscopy to analyze erase kinetics.

Microscopic Image Capture: Samples are imaged in flow cells consisting of coverslip or slide mounted samples, a spacer (double-sided tape), and a top coverslip, as we described previously [Mahajan, K. D., et al. Nanoscale 2016 8(16):8641-9]. Solution exchanges (e.g., labels, erase DNA, antifade reagents and buffers) flow into the system initially using pipetting, and ultimately, via syringe pump. Flow cells are compatible with standard inverted confocal microscopes, permitting broad adoption. Images will be collected using an Olympus IX-71 inverted, spinning disk confocal microscope equipped with Metamorph software and color and EMCDD cameras. Additional imaging configurations are possible, the flow cell is thus not limiting.

This technology was used to label integrin P1 in fibroblasts (FIG. 5C), demonstrating feasibility of our approach (~120 s for erasable labels vs. ~190 s for photobleach alone). Unfortunately, in these initial experiments, the dye used for cell labeling was attached to the surface of the DNA cage, rather than encapsulated in the particle. Thus, photobleaching of the dye occurred simultaneously with erase. Nonetheless, fluorescence was reduced by 80% in 80 s vs. 110 s for photobleach alone. Thus, DNA cages can be used as erasable labels.

Figure 9:
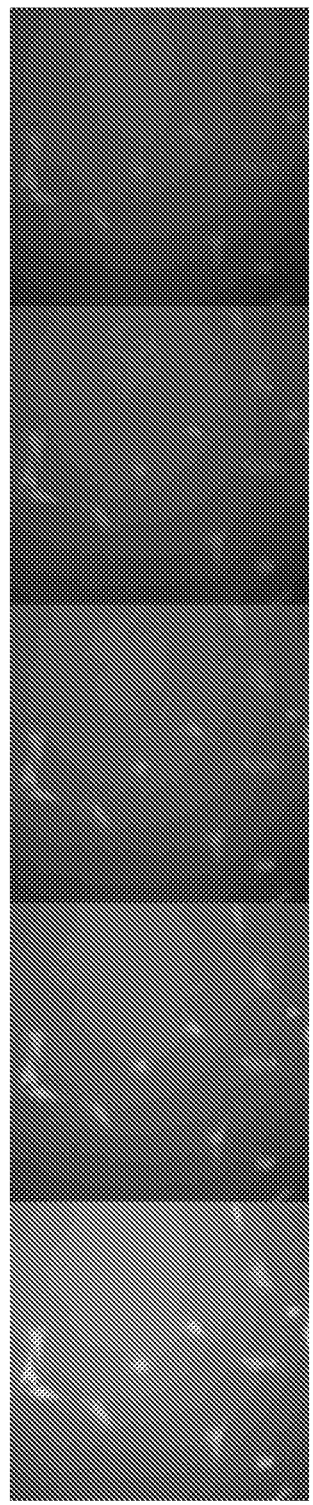
FIG. 9 shows $β_1$ integrin labeling in fibroblast cells. In these experiments, coumarin-6 fluorophores were encapsulated inside DNA caged micelles. Each frame represents the passage of 4 minutes. Fluorescence was diminished by 50% after 20 minutes of exposure.
Figure 10:
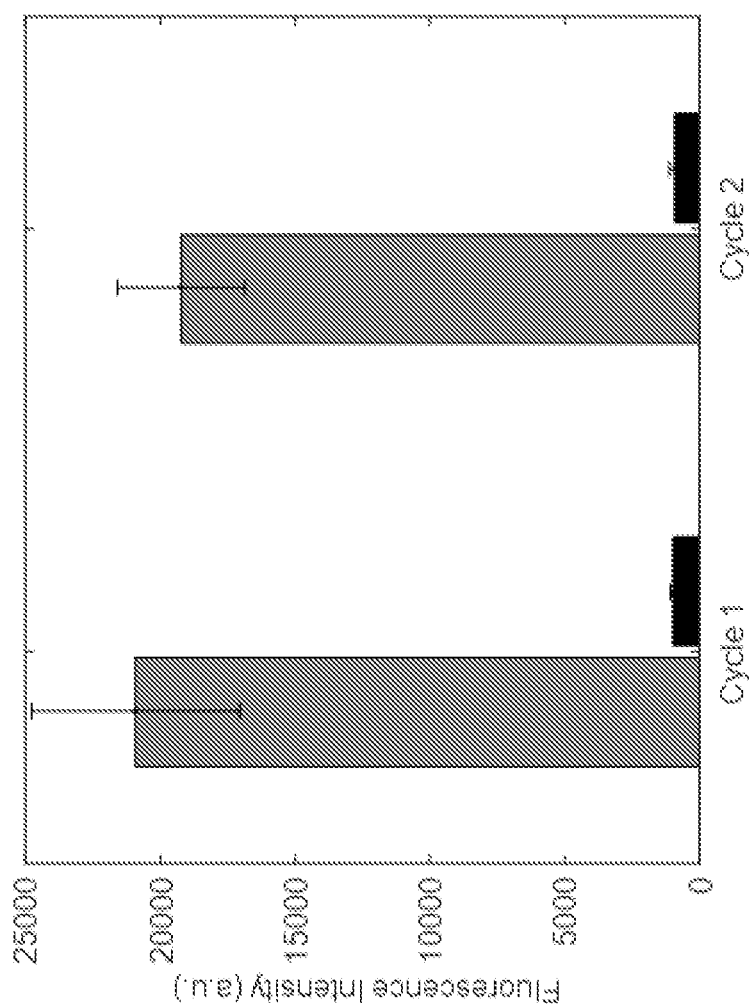
FIG. 10 shows Erasable labeling using DNA cages in solution. ssDNA targeting strands on cages were labeled using complementary ssDNA tagged with Cy5. Upon binding, signal increases (gray); with addition of untagged complementary DNA signal declines (black). Cycle 1 used complementary ssDNA with 9 bps, and a 12 bp erase strand, whereas Cycle 2 used a 15 bp complimentary strand, and a 26 bp complimentary erase strand.

This experiment was also repeated using DNA caged nanoparticles encapsulating coumarin-6 fluorophore dye (FIG. 9). In this case, the fluorophore was photo-protected inside the particle. This signal was monitored for 20 min, and there was a 50% reduction in fluorescence (e.g., erase) over this time. Performance can be improved by direct conjugation to primary antibodies (reduces cross talk and non-specific binding) and through optimization of the ssDNA targeting sequence length.

Example 3: Erasable Labels for Tissue Histology

In this example, technologies and methods using DNA-cage labels for tissue histology are disclosed. This example focuses specifically on multiplexed imaging, although embodiments in which single color/wavelength DNA cage labels are used in a single or repeated cycle(s) are also possible. These labels are then used to develop multiplexed labeling technologies and methods compatible with standard fluorescence and upright microscopes.

Methods: DNA-Cage labels: Labels are synthesized using particles containing differently-colored QDs (CdS/ZnS 400, 425, or 450 nm; CdSe/ZnS 520, 540, 560, 580, 600, or 620 nm emission, Ocean Nanotech) as described previously [Nabar, G. M., et al. Inter J Nanomed 2018 13:351-366; Duong, A. D., et al. Langmuir 2014 30(14):3939-3948] and in Example 1. Fluorophores or chromophores are employed as an alternative approach.

Tissue Labeling: Tissue sections are permeabilized for 20 minutes in 0.05 M PBS with 0.1% Triton™ X-100 at room temperature. Antigen retrieval is performed with 10 mM citrate buffer pH 6.0 at 95° C. for 20 minutes. Blocking is performed by 2-hour incubation in 0.05 M PBS, 0.1% Triton™ X-100 (v/v), 5% normal goat serum (v/v) (ThermoFisher Scientific #10000C) and 1% bovine serum albumin (w/v) (Fisher). Standard avidin/biotin labeling procedures are employed as described above and as used in FIG. 5 and FIG. 9. Tissues are imaged as described above via time-lapse confocal fluorescence microscopy.

This technology has the potential to impact many fields by providing a flexible paradigm for repeated chromophore, fluorophore, or QD-labeling in histological specimens. Labeling protocols are developed for application in serial (leveraging single-label epitope retrieval approaches) or parallel (increasing multiplexing), enabling efficient adoption by researchers. Such a platform addresses challenges of spatially overlapping signals [Ghaznavi, F., et al., Digital Imaging in Pathology: Whole-Slide Imaging and Beyond, in Annual Review of Pathology: Mechanisms of Disease, Vol 8, Abbas, A. K., et al., Editors. 2013. p. 331-359] by enabling use of multiple labels with similar spectral signatures. These approaches are compatible with a variety of tissue processing methods, including flash frozen, formalin fixed paraffin embedded, and optically cleared [Dodt, H. U., et al. Nature Methods 2007 4(4):331-336] tissues. They can be implemented across many platforms, including brightfield, fluorescence, digital, whole-slide, and multispectral imaging, enhancing their capabilities. This technology is also compatible with commercial erasable multiplexing systems [Gerdes, M. J., et al. Proc Natl Acad Sci USA. 2013 110(29):11982-11987; EP0810428B1], replacing potentially tissue damaging methods by bio-friendly DNA interactions.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A labeling system, comprising
a nanocage assembly comprising a nanoparticle loaded with one or a plurality of imaging agents that is encapsulated by a DNA or RNA nanocage,
a single stranded oligonucleotide erasing molecule, and
optionally a plurality of single stranded oligonucleotide targeting molecules,
wherein the nanocage comprises a plurality of single stranded DNA (ssDNA) or single stranded RNA (ssRNA) targeting arms,
wherein the targeting arms are complementary to both the erasing molecule and either a DNA or RNA target or the targeting oligonucleotide, but has a higher complementarity and affinity for the oligonucleotide erasing molecule, or wherein either the DNA or RNA target or the targeting molecule comprises a nucleic acid sequence that is complementary to both the targeting arm and the erasing molecule but has a higher complementarity and affinity for the oligonucleotide erasing molecule.

2. The system of claim 1, wherein the targeting molecule is conjugated to a targeting agent.

3. The system of claim 2, wherein the targeting agent is an antibody or aptamer.

4. The system of claim 1, wherein the nanocage comprises a plurality of DNA or RNA oligomers, wherein each oligomer comprises at least three ssDNA oligonucleotides self-assembled to form at least three arms, wherein at least two of the arms terminate as ssDNA sticky ends that are complementary to each other, wherein the nanocage comprises a plurality of the oligomers linked by the sticky ends, and wherein a portion of the oligomers comprise at least one arm that terminates as the targeting arm.

5. The system of claim 4, wherein the portion of oligomers that comprise at least one are that terminates as the targeting arm comprises about 1%, 2%, 3%, 4%, 5%, 6%, 7%, 8%, 9%, 10%, 15%, 20%, 25%, 30%, 35%, 40%, 45%, 50% or more of the total oligomers.

6. The system of claim 1, wherein the imaging agent comprises a chromophore, fluorophore, or quantum dot.

7. A method for labeling of a sample, comprising
 (a) providing a first nanocage assembly comprising a nanoparticle loaded with, bound to, or adsorbed with an imaging agent and encapsulated in a DNA or RNA nanocage, wherein the nanocage comprises a first targeting arm that selectively binds a first DNA or RNA target;
 (b) providing a second nanocage assembly comprising a nanoparticle loaded with, bound to, or adsorbed with an imaging agent and encapsulated in a DNA or RNA nanocage, wherein the nanocage comprises a second targeting arm that selectively binds a second DNA or RNA target;
 (c) providing a first oligonucleotide erasing molecule comprising a nucleic acid sequence that is complementary to either the first DNA or RNA target or the first targeting arm;
 (d) optionally providing a second oligonucleotide erasing molecule comprising a nucleic acid sequence that is complementary to either the second DNA or RNA target or the second targeting arm;
 (e) contacting the sample with the first nanocage assembly under conditions suitable for binding of the targeting arm of the first nanocage assembly to the first DNA or RNA target;
 (f) imaging the sample for the imaging agents;
 (g) contacting the sample with the first erasing molecule under conditions suitable for binding of the erasing molecule to either the first DNA or RNA target or the first targeting arm;
 (h) washing away the first nanocage assembly;
 (i) contacting the sample with the second nanocage assembly under conditions suitable for binding of the targeting arm of the second nanocage assembly to the second DNA or RNA target;
 (j) imaging the sample for the imaging agents;
 (k) optionally contacting the sample with the second erasing molecule under conditions suitable for binding of the erasing molecule to either the second DNA or RNA target or the second targeting arm; and
 (l) optionally washing away the second nanocage assembly.

8. A method for labeling of a sample, comprising
 (a) providing a first targeting agent that selectively binds a first target in the sample, wherein the first targeting agent is conjugated to a first single stranded oligonucleotide targeting molecule;
 (b) providing a second targeting agent that selectively binds a second target in the sample, wherein the second targeting agent is conjugated to a second single stranded oligonucleotide targeting molecule;
 (c) providing a first nanocage assembly comprising a nanoparticle loaded with, bound to, or adsorbed with an imaging agent and encapsulated in a DNA or RNA nanocage, wherein the nanocage comprises a first targeting arm that selectively binds the first targeting molecule;
 (d) providing a second nanocage assembly comprising a nanoparticle loaded with, bound to, or adsorbed with an imaging agent and encapsulated in a DNA or RNA nanocage, wherein the nanocage comprises a second targeting arm that selectively binds the second targeting molecule;
 (e) providing a first oligonucleotide erasing molecule comprising a nucleic acid sequence that is complementary to either the first targeting molecule or the first targeting arm;
 (f) optionally providing a second oligonucleotide erasing molecule comprising a nucleic acid sequence that is complementary to either the second targeting molecule or the second targeting arm;
 (g) contacting the sample with the first targeting agent under conditions suitable for the first targeting agent to selectively bind the first target in the sample;
 (h) contacting the sample with a second targeting agent under conditions suitable for the second targeting agent to selectively bind the second target in the sample;
 (i) contacting the sample with the first nanocage assembly under conditions suitable for binding of the targeting arm of the first nanocage assembly to the targeting molecule of the first targeting agent;
 (j) imaging the sample for the imaging agents;
 (k) contacting the sample with the first erasing molecule under conditions suitable for binding of the erasing molecule to either the first targeting molecule or the first targeting arm;
 (l) washing away the first nanocage assembly;
 (m) contacting the sample with the second nanocage assembly under conditions suitable for binding of the targeting arm of the second nanocage assembly to the targeting molecule of the second targeting agent;
 (n) imaging the sample for the imaging agents;
 (o) optionally contacting the sample with the second erasing molecule under conditions suitable for binding of the erasing molecule to either the second targeting molecule or the second targeting arm; and
 (p) optionally washing away the second nanocage assembly.

9. The method of claim 6, further comprising
 (a) providing a third targeting agent that selectively binds a third target in the sample, wherein the third targeting agent is conjugated to a third single stranded oligonucleotide targeting molecule;
 (b) providing a third nanocage assembly comprising a nanoparticle loaded with, bound to, or adsorbed with one or a plurality of imaging agents and encapsulated in a DNA or RNA nanocage, wherein the nanocage comprises a third targeting arm that selectively binds the third targeting molecule;

(c) optionally providing a third erasing molecule comprising a nucleic acid sequence that is complementary to either the third targeting molecule or the third targeting arm;

(d) contacting the sample with a third targeting agent under conditions suitable for the third targeting agent to selectively bind the third target in the sample;

(e) contacting the sample with the third nanocage assembly under conditions suitable for binding of the targeting arm of the third nanocage assembly to the targeting molecule of the third targeting agent;

(f) imaging the sample for the imaging agents;

(g) optionally contacting the sample with the third erasing molecule under conditions suitable for binding of the erasing molecule to either the third targeting molecule or the third targeting arm; and (h) optionally washing away the third nanocage assembly.

* * * * *

SEQUENCE LISTING

<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Synthetic Construct

<400> SEQUENCE: 1
cagtgaggac ggaagtttgt cgtagcatcg cacc        34

<210> SEQ ID NO 2
<211> LENGTH: 42
<212> TYPE: DNA
<213> ORGANISM: Artificial Sequence
<220> FEATURE:
<223> OTHER INFORMATION: Synthetic Construct

<400> SEQUENCE: 2
gctcgagcca accacgcctg tccattactt ccgtcctcac tg        42

<210> SEQ ID NO 3
<211> LENGTH: 42
<212> TYPE: DNA
<213> ORGANISM: Artificial Sequence
<220> FEATURE:
<223> OTHER INFORMATION: Synthetic Construct

<400> SEQUENCE: 3
gctcgagcgg tgcgatgcta cgactttgga caggcgtggt tg        42

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4
gattatcaaa gaggtgcatg taacgtcg        28

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
aaaaatttcg acgttacatg cacc        24